(12) United States Patent
Nielsen et al.

(10) Patent No.: US 11,065,144 B2
(45) Date of Patent: Jul. 20, 2021

(54) OSTOMY POUCH WITH NIGHT DRAINAGE ADAPTER

(71) Applicant: Hollister Incorporated, Libertyville, IL (US)

(72) Inventors: Kenneth Nielsen, Alsgarde (DK); Jan Torstensen, Virum (DK); Christen Grum-Schwensen, Gadevang (DK); Mette Dybendal Maack, Lyngby (DK); Sussie Richmann, Hellebaek (DK); Jan Wohlgemuth, Horsholm (DK); Peter Moller-Jensen, Hornbaek (DK); Ole Skjodt, Rungsted Kyst (DK)

(73) Assignee: Hollister Incorporated, Libertyville, IL (US)

( * ) Notice: Subject to any disclaimer, the term of this patent is extended or adjusted under 35 U.S.C. 154(b) by 397 days.

(21) Appl. No.: 16/033,919

(22) Filed: Jul. 12, 2018

(65) Prior Publication Data

US 2018/0318127 A1 Nov. 8, 2018

Related U.S. Application Data

(63) Continuation of application No. PCT/US2017/015767, filed on Jan. 31, 2017.

(Continued)

(51) Int. Cl.
*A61F 5/44* (2006.01)
*A61F 5/445* (2006.01)
*A61F 5/448* (2006.01)

(52) U.S. Cl.
CPC .......... *A61F 5/4407* (2013.01); *A61F 5/4404* (2013.01); *A61F 5/445* (2013.01); *A61F 2005/4486* (2013.01)

(58) Field of Classification Search
CPC ............... A61F 5/4407; A61F 5/455; A61F 2005/4486; A61F 5/44; A61F 5/4404;
(Continued)

(56) References Cited

U.S. PATENT DOCUMENTS 3,523,534 A 8/1970 Nolan
3,690,320 A * 9/1972 Riely ....................... A61F 5/441
604/333

(Continued)

FOREIGN PATENT DOCUMENTS

EP 0276917 A1 8/1988
EP 1749507 A2 2/2007
(Continued)

OTHER PUBLICATIONS

International Search Report issued by ISA/EPO in connection with PCT/US2017/015767 dated Jul. 11, 2017.
(Continued)

*Primary Examiner* — Tatyana Zalukaeva
*Assistant Examiner* — Heather K Barnwell
(74) *Attorney, Agent, or Firm* — Levenfeld Pearlstein, LLC

(57) ABSTRACT

An ostomy pouch includes a collection pouch having a first side wall and a second side wall connected to one another along a periphery, the collection pouch having a collection cavity defined between the first and second side walls, an outlet connected to and extending from the collection pouch, the outlet defining an internal passageway connected to the collection cavity, the outlet having a coupling element, and a drainage adapter configured to engage the coupling element so as to be coupled to the outlet. The outlet is foldable to a closed condition to close the collection pouch and unfoldable to an open condition to drain the collection pouch.

7 Claims, 4 Drawing Sheets

Related U.S. Application Data

(60) Provisional application No. 62/291,993, filed on Feb. 5, 2016.

(58) Field of Classification Search
CPC ........ A61F 5/4408; A61F 5/442; A61F 5/448; A61F 2005/4483
See application file for complete search history.

(56) References Cited

U.S. PATENT DOCUMENTS

| | | | | |
|---|---|---|---|---|
| 3,825,005 | A | * | 7/1974 | Fenton ................ A61F 5/4407 604/335 |
| 3,841,332 | A | * | 10/1974 | Treacle ................ A61F 5/445 604/335 |
| 4,411,659 | A | | 10/1983 | Jensen et al. |
| 5,495,858 | A | * | 3/1996 | Steer ................ A61F 5/448 128/885 |
| 5,951,532 | A | | 9/1999 | Olsen |
| 7,947,025 | B2 | * | 5/2011 | Buglino ................ A61F 5/445 604/335 |
| 2006/0106354 | A1 | | 5/2006 | Vantroostenberghe |

FOREIGN PATENT DOCUMENTS

| | | |
|---|---|---|
| WO | 2006031275 A2 | 3/2006 |
| WO | 2008141652 A1 | 11/2008 |

OTHER PUBLICATIONS

Written Opinion issued by ISA/EPO in connection with PCT/US2017/015767 dated Jul. 11, 2017.

International Preliminary Report on Patentability issued by International Bureau of WIPO in connection with PCT/US2017/015767 dated Aug. 7, 2018.

* cited by examiner

OSTOMY POUCH WITH NIGHT DRAINAGE ADAPTER

CROSS-REFERENCE TO RELATED APPLICATION DATA

The present application is a continuation of International Application No. PCT/2017/015767, filed Jan. 31, 2017, titled Ostomy Pouch With Night Drainage Adapter, which claims the benefit of and priority to U.S. Provisional Patent Application No. 62/291,993, filed Feb. 5, 2016, titled Ostomy Pouch With Night Drainage Adapter, the disclosures of which are incorporated herein in their entireties.

BACKGROUND

The following description generally relates to ostomy appliances, and in particular, an ostomy pouch having a night drainage adapter.

Ostomy pouches for collecting body waste are used by patients who have had surgery such as a colostomy, ileostomy, or urostomy. Ostomy pouches typically include flat, opposing side walls secured together along their edges to define a collection cavity. One of the side walls is provided with an opening to receive a stoma, and means to secure the pouch to the user, such as an adhesive barrier, so that body waste discharged through the stoma is received within the cavity without leakage outside of the stoma/barrier/pouch environment.

The ostomy pouch may be a drainable pouch having a discharge opening at a lower end. The discharge opening may be closed during collection of body waste material, but may be opened to drain the waste material from the pouch. Such drainable ostomy pouches are disclosed, for example, in Nolan, U.S. Pat. No. 3,523,534, and Jensen et al., U.S. Pat. No. 4,411,659, which are incorporated herein by reference in their entirety.

The discharge opening of drainable ostomy pouches is typically defined at the end of a narrowed neck portion, which is provided with closure means for maintaining the discharge opening in a sealed condition until waste material is to be drained from the pouch. The closure means may take the form of a clamp, as in the aforementioned Nolan patent, or a device such as conventional wire tires or wraps for securing the neck portion in an upwardly-rolled condition.

In daily use, bodily waste may accumulate in the ostomy pouch. Accordingly, the ostomy pouch needs to be drained on occasion. Bodily waste may be drained from the ostomy pouch by opening the discharge opening. For example, in an ostomy pouch having an upwardly-rolled neck to close the discharge opening, the neck may be unrolled to release the bodily waste. However, for night use, such occasional draining may not be convenient for the patient as it may interrupt sleep.

To address this, some ostomy pouches are equipped to be attached to a night drainage system. A night drainage system may include a hose or tube to be coupled to the discharge opening at one end and a night reservoir at the other end. The night reservoir is of a sufficient volume to collect bodily waste through the night without needing to be drained.

However, the ostomy pouches having the upwardly-foldable closures are not suitable for attachment to night drainage systems, as they lack an adequate coupling surface, in favor of flexibility to allow for folding. Thus, to prepare for night use, a patient must remove the ostomy pouch having the upwardly-foldable closure and replace it with an ostomy pouch having a discharge opening suitable for coupling to night drainage system. Replacing ostomy pouches on the patient's body may be time consuming, labor intensive and inconvenient. In addition, removing and replacing ostomy pouches on the patient's body may cause irritation in the peristomal area.

Accordingly, it is desirable to provide a drainable ostomy pouch having a foldable outlet suitable for connection to a night drainage system.

SUMMARY

According to one embodiment, there is provided an ostomy pouch including a collection pouch having a first side wall and a second side wall connected to one another along a periphery, the collection pouch having a collection cavity defined between the first and second side walls, an outlet connected to and extending from the collection pouch, the outlet defining an internal passageway connected to the collection cavity, the outlet having a coupling element, and a drainage adapter configured to engage the coupling element so as to be coupled to the outlet. The outlet is foldable to a closed condition to close the collection pouch and unfoldable to an open condition to drain the collection pouch.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
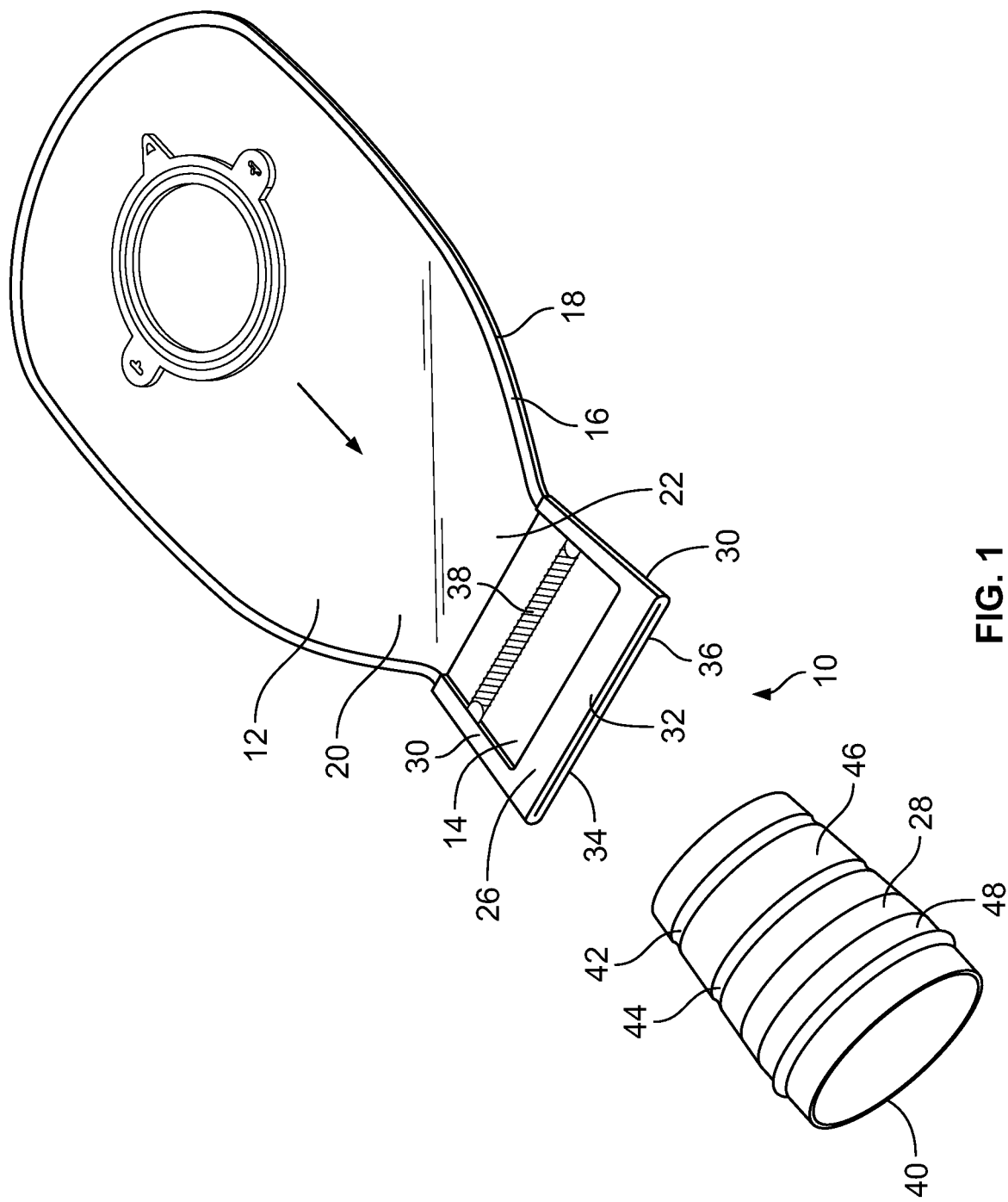
FIG. 1 is a perspective view of an ostomy pouch according to an embodiment described herein.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Referring generally to FIGS. 1-4, the embodiments described herein include an ostomy pouch 10 having a collection pouch 12 and an outlet 14. The collection pouch 12 may generally be formed by a first side wall 16 and a second side wall 18 joined to one another at a periphery, or integrally connected with one another as a single unit. A collection cavity 20 is defined within the collection pouch 12, i.e., between the first and second side walls 16, 18. The collection pouch 12 also includes an inlet (not shown) formed in one of the side walls 16, 18 configured to receive stoma so that a discharge from the stoma may be received from the stoma in the collection cavity 20. The inlet may be positioned at an upper portion of the collection pouch 12. The collection pouch 12 further includes a discharge port 22 configured for connection to the outlet 14. The discharge port 22 may be, for example, an opening formed in the periphery or one of the side walls 16, 18, and may be disposed at a lower portion of the collection pouch 12.

In one embodiment, the outlet 14 may be formed as a single, continuous part, for example, in a molding process. The outlet 14 includes an internal passageway 24 (see, for example, FIG. 2) connected to the collection cavity 20 so that contents may flow from the collection cavity 20 into the internal passageway 24. In one embodiment, the outlet 14 may be formed separately from the collection pouch 12 and connected to the collection pouch 12 at the discharge port 22. The outlet 14 may be connected to the collection pouch 12 in any suitable manner that seals the outlet 14 to the collection pouch 12 such that contents flow from the collection cavity 20 to the internal passageway 24 without leaking. For example, the outlet 14 may be heat sealed, welded, or the like, to the collection pouch 12. In other embodiments, the outlet 14 may be formed integrally and continuously with the collection pouch 12. The outlet 14 may be formed having a narrowed neck portion relative to the collection pouch 12.

In one embodiment, the outlet 14 may also be a closure member configured to close and/seal the collection cavity 20 of the collection pouch 12 to limit or prevent inadvertent leakage of the contents from the collection cavity. For example, the outlet 14 may be folded or rolled one or more times to close or seal the internal passageway 24 to, in turn, close or seal the collection cavity 20 to prevent egress of the contents thereof. The outlet 14 may be held in a closed condition with a suitable fastener (not shown).

Referring to FIG. 1, in one embodiment, the outlet 14 includes a coupling element 26. The coupling element 26 may be formed integrally and continuously with the outlet 14. For example, the coupling element 26 may be formed as a section of increased thickness in a predetermined shape and configuration for coupling to a drainage adapter 28, described further below. Alternatively, the coupling element 26 may be formed separately from the outlet 14 and secured thereto. For example, the coupling element 26 may be secured to outlet 14 within the internal passageway 24, and sealed against an interior wall of the outlet 14.

In one embodiment, the coupling element 26 generally includes laterally spaced apart legs 30 and a grip 32 extending between the legs 30. The grip 32 may be positioned substantially at a distal end 34 of the outlet 14, at a location corresponding to a discharge end of the outlet 14. Alternatively, the grip 32, or free end of the coupling element 26 may be positioned within the outlet 14 and may serve as a support about which the outlet 14 may be folded to be closed. The grip 32 includes a slit 36 connected to the internal passageway 24. The coupling element 26 also includes a pouch sealing band 38 extending between the legs 30. The pouch sealing band 38 is positioned between the grip 32 and the collection pouch 12.

The coupling element 26 may be formed from an elastically deformable material. In one embodiment, the elastically deformable material urges the slit 36 and the pouch sealing band 38 toward a closed position. The coupling element 26 may be biased under an intrinsic spring force of the elastically deformable material or by an auxiliary biasing element, such as a leaf spring or other similar spring.

Referring still to FIG. 1, the drainage adapter 28 defines an internal adapter passageway 40 configured for connection to the internal passageway 24 of the outlet 14 and the collection cavity 20. The drainage adapter 28 also includes a first groove 42 and a second groove 44. The first and second grooves 42, 44 are externally positioned on the drainage adapter 28 and, in one embodiment, extend completely about an outer periphery of the drainage adapter 28.

The drainage adapter 28 includes a first segment 46 and a second segment 48 positioned in series along its length. The first segment 46 is configured to be coupled to the coupling element 26 and the second segment 48 is configured to extend outwardly from the coupling element 26 and the outlet 14 when coupled thereto. In one embodiment, at least a portion of the first segment 46 is configured to be received within the outlet 14 and the coupling element 26, while the second segment 48 is configured to extend outward and externally from the outlet 14 and first coupling element. A hose or tube (not shown) of the night drainage system may be attached to the second segment 48. The first and second grooves 42, 44 may be formed on the first segment 46. A width of the drainage adapter 28 may be tapered so as to decrease when moving along at least portion of the length toward a leading end of the adapter 28 to be inserted into the outlet 14.

Figure 2:
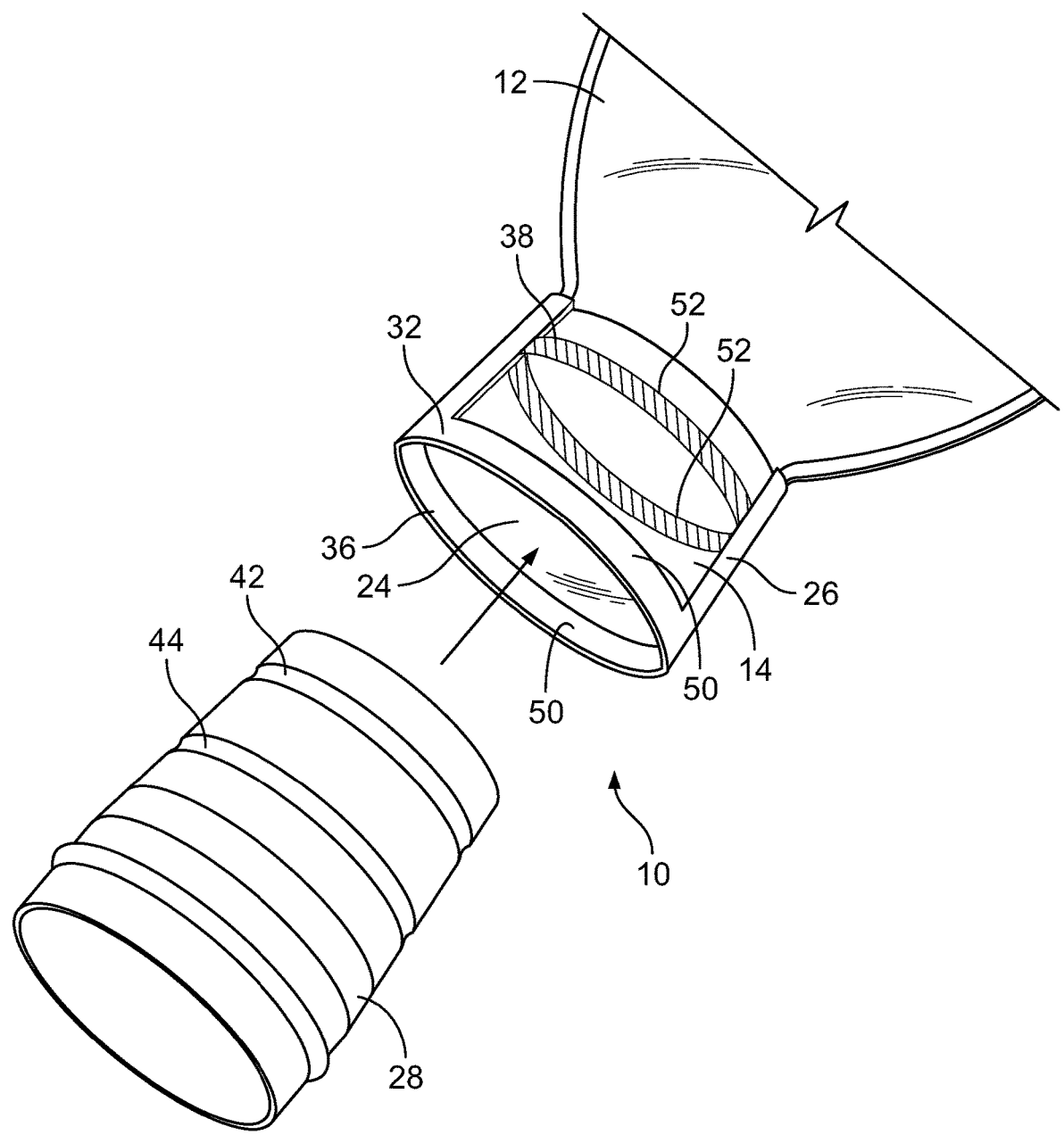
FIG. 2 is a perspective view of the ostomy pouch of FIG. 1 configured to receive a drainage adapter in an outlet, according to an embodiment described herein.

FIG. 2 shows the ostomy pouch 10 in a position where the drainage adapter 28 may be coupled to the coupling element 26, according to an embodiment described herein. Referring to FIG. 2, the coupling element 26 may be moved from a closed position to an open position, where both the slit 36 and the pouch sealing band 38 are moved to an open position. Movement from the closed position to the open position may be accommodated, for example, by applying opposing, inwardly directed forces on the laterally spaced legs 30 (FIG. 1) to elastically deform the coupling element 26.

In one embodiment, the slit 36 may be defined by oppositely positioned sections 50 of the grip 32. Similarly, in one embodiment, the pouch sealing band 38 may include oppositely positioned first and second bands 52. In the closed position, as shown in FIG. 1, the oppositely positioned grip sections 50 are urged toward one another to substantially or completely close the slit 36. Similarly, the first and second bands 52 are urged toward one another in the closed position. Referring to FIG. 2, in the open position, the oppositely positioned sections 50 of the grip 32 are deflected away from another. Likewise, in the open position, the oppositely positioned first and second bands 52 are deflected away from one another. Accordingly, in one embodiment, the drainage adapter 28 may be received in the outlet 14 with the coupling element 26 in the open position and coupled to the outlet 14 via the coupling element 26.

Figure 3:
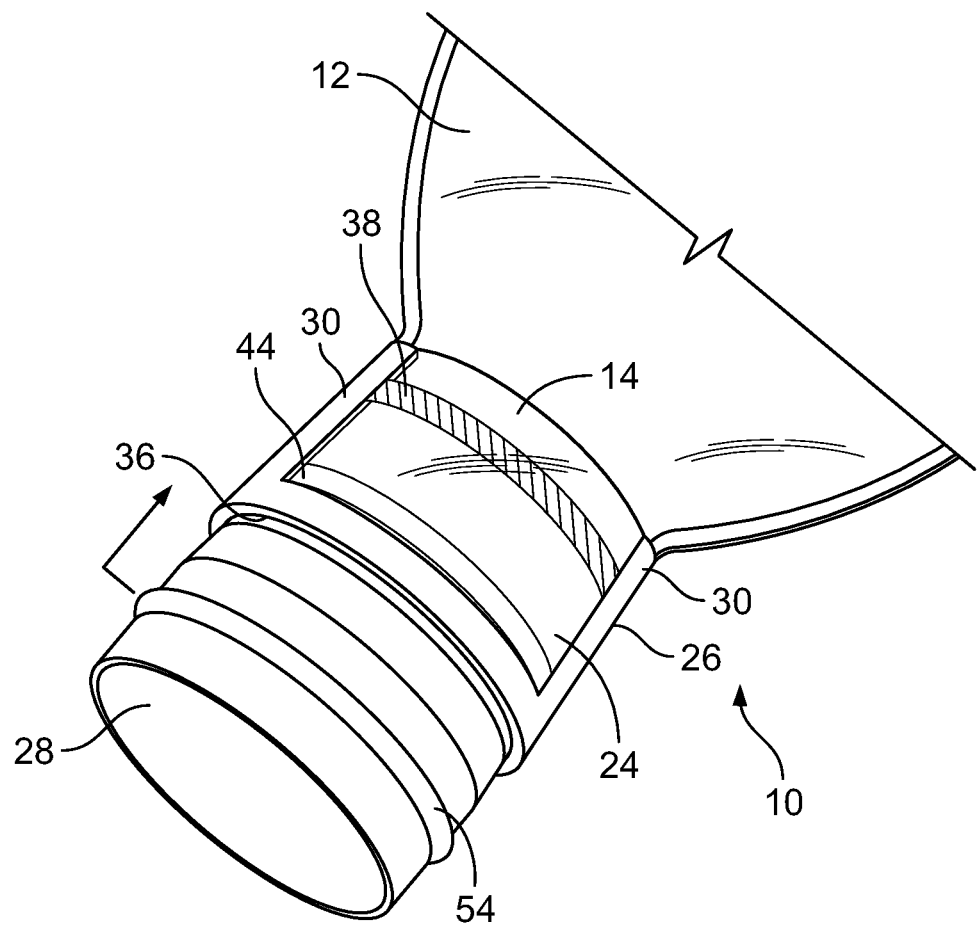
FIG. 3 is a perspective view of the ostomy pouch of FIG. 1 having the drainage adapter partially installed in the outlet according to an embodiment described herein.

FIG. 3 shows the drainage adapter 28 received in and partially coupled to the coupling element 26 of the outlet 14, according to an embodiment described herein. Referring to FIG. 3, the drainage adapter 28 may be received through the opened slit 36 and the pouch sealing band 38 such that the drainage adapter 28 is positioned in the internal passageway 24. In this position, the pouch sealing band 38 is received in the first groove 42 such that the coupling element 26 and the outlet 14 are sealed to the drainage adapter 28 at a position on the first segment of the drainage adapter 28. In one embodiment, the pouch sealing band 38 is urged into and held in sealing contact against the drainage adapter 28, and in particular, in the first groove 42, under the spring force of the material from which the first coupling member is formed. Further, the laterally spaced legs 30 may also seal against the drainage adapter 28.

Referring still to FIG. 3, in one embodiment, the ostomy pouch 10 may also include locking element 54, for example, in the form of an O-ring. The locking element 54 may initially be disposed on the second segment 48 of the drainage adapter 28 and is configured to be received in the second groove 44 of the drainage adapter 28 as discussed below.

Figure 4:
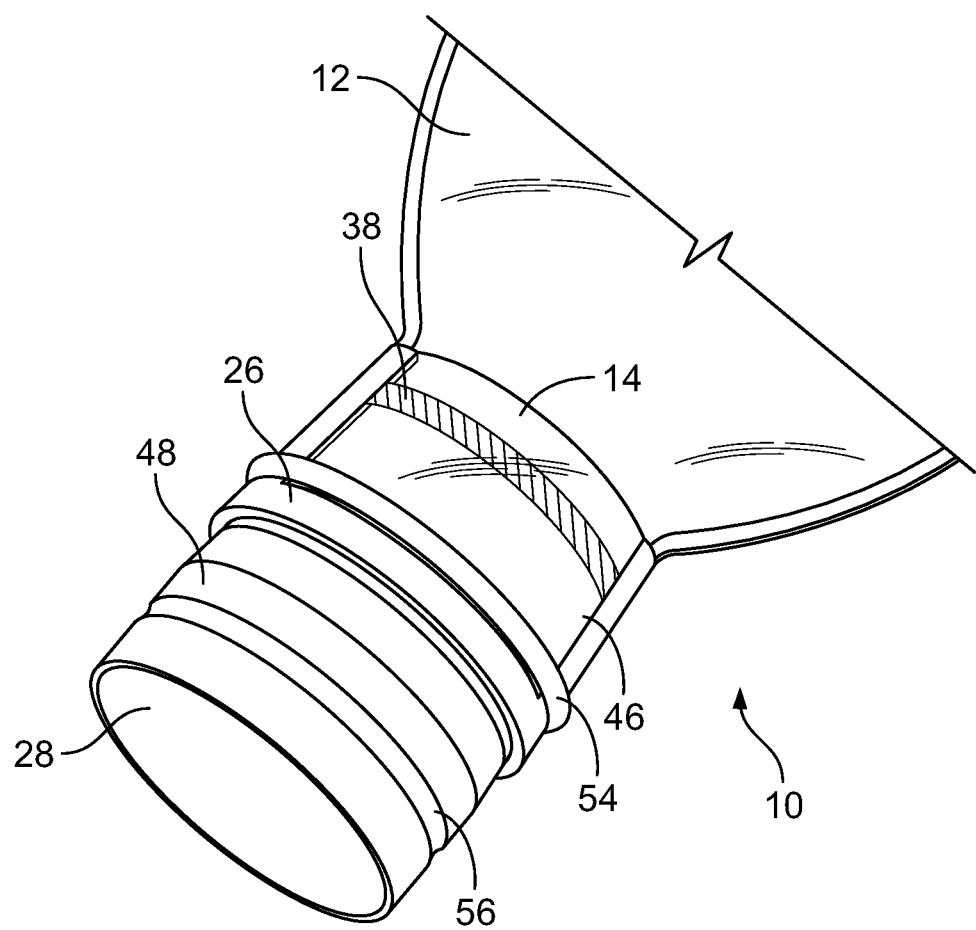
FIG. 4 is a perspective view of the ostomy pouch of FIG. 1 having a drainage adapter fully installed in the outlet, according to an embodiment described herein.

FIG. 4 shows the drainage adapter 28 coupled to the coupling element 26 of the outlet 14 and ready for use with a night drainage system (not shown), according to an embodiment described herein. Referring to FIG. 4, in one embodiment, the drainage adapter 28 may further include a third groove 56 where the locking element 54 may be initially positioned and held when the drainage adapter 28 is not in use. With the drainage adapter 28 installed in the coupling element 26, the locking element 54 may be moved from the third groove 56 to the second groove 44 (see FIG. 3). In this position, the locking element 54 may extend around the outlet 14, the coupling element 26 and the drainage adapter 28 to secure the assembly together against inadvertent removal from the collection bag 12. In addition, the locking element 56 may form another seal against the drainage adapter 28.

Accordingly, in the embodiments above, an ostomy pouch may include a collection pouch having a foldable outlet that is folded to close and/or seal the collection pouch in daily use, and unfolded to drain or empty the collection pouch. The ostomy pouch further includes a drainage adapter configured for use with the foldable outlet to connect the ostomy pouch to a night drainage system. The adapter is sealingly connected to the outlet by way of a coupling element, and is further secured to the outlet by way of a locking element, such as an O-ring. Thus, the ostomy pouch having a foldable outlet may be securely connected to a night drainage bag or system. Contents of the collection pouch may flow through the internal passageway of the outlet, into the adapter internal passageway, and ultimately into the night drainage bag or system. In the embodiments above, both the outlet and the adapter may be injection molded. However, other suitable manufacturing processes may be employed as well.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy pouch comprising:
   a collection pouch having a first side wall and a second side wall connected to one another along a periphery, the collection pouch having a collection cavity defined between the first and second side walls;
   an outlet connected to and extending from the collection pouch, the outlet defining an internal passageway connected to the collection cavity, the outlet having a coupling element, wherein the coupling element includes a pouch sealing band configured to sealingly engage a drainage adapter; and
   the drainage adapter configured to engage the coupling element so as to be coupled to the outlet, wherein the drainage adapter includes a first groove and a second groove, wherein the first groove is configured to receive the pouch sealing band, wherein the pouch sealing band is urged into and held in sealing contact against the drainage adapter in the first groove under a spring force of a material from which the pouch sealing band is formed; and
   a locking element (54) configured to fit around the drainage adapter (28), wherein the second groove (44) is configured to receive the locking element,
   wherein the outlet is foldable to a closed condition to close the collection pouch and unfoldable to an open condition to drain the collection pouch.

2. The ostomy pouch of claim 1, wherein the locking element is an O-ring.

3. The ostomy pouch of claim 1, wherein the locking element is movable from a first position on the drainage adapter to a second position where the locking element fits over the drainage adapter, the coupling element and the outlet.

4. The ostomy pouch of claim 3, wherein the drainage adapter further includes a third groove configured to receive the locking element in the first position.

5. The ostomy pouch of claim 1, wherein the drainage adapter has a first segment received within the coupling element.

6. The ostomy pouch of claim 5, wherein the drainage adapter has a second segment extending from the coupling element.

7. The ostomy pouch of claim 1, wherein the coupling element further includes laterally spaced apart legs, a grip having a slit formed therein extending between the legs, and a pouch sealing band configured to sealingly engage the drainage adapter.

* * * * *